US012616430B2

(12) United States Patent (10) Patent No.: US 12,616,430 B2
Michel (45) Date of Patent: May 5, 2026

(54) ELECTRIC CIRCUITRY FOR BASELINE EXTRACTION IN A PHOTON COUNTING SYSTEM

(71) Applicant: ams International AG, Jona (CH)

(72) Inventor: Fridolin Michel, Au (CH)

(73) Assignee: AMS INTERNATIONAL AG, Jona (CH)

( * ) Notice: Subject to any disclaimer, the term of this patent is extended or adjusted under 35 U.S.C. 154(b) by 154 days.

(21) Appl. No.: 18/256,066

(22) PCT Filed: Dec. 2, 2021

(86) PCT No.: PCT/EP2021/083967
§ 371 (c)(1),
(2) Date: Jun. 6, 2023

(87) PCT Pub. No.: WO2022/122545
PCT Pub. Date: Jun. 16, 2022

(65) Prior Publication Data
US 2024/0036219 A1 Feb. 1, 2024

(30) Foreign Application Priority Data

Dec. 9, 2020 (DE) .......................... 102020132798.6

(51) Int. Cl.
*A61B 6/42* (2024.01)
*A61B 6/00* (2006.01)
(Continued)

(52) U.S. Cl.
CPC ............ *A61B 6/4241* (2013.01); *A61B 6/482* (2013.01); *G01T 1/178* (2013.01); *G01T 1/247* (2013.01); *G01T 1/2928* (2013.01)

(58) Field of Classification Search
CPC ....... A61B 60/032; A61B 6/035; A61B 6/037; A61B 6/42; A61B 6/4208; A61B 6/4233;
(Continued)

(56) References Cited

U.S. PATENT DOCUMENTS 5,943,388 A * 8/1999 Tümer ................... G01V 5/226
378/98.9
6,248,990 B1 * 6/2001 Pyyhtiä ................ H04N 25/773
250/370.08
(Continued)

FOREIGN PATENT DOCUMENTS

CN 108 291 971 A 7/2018
JP 2014530704 A 11/2014

OTHER PUBLICATIONS

Nakao, T., Notice of Reasons for Refusal issued in corresponding Japanese Patent Application No. 2023-558938 dated Jul. 26, 2024, with English language translation, 15 pages.
(Continued)

*Primary Examiner* — Allen C. Ho
(74) *Attorney, Agent, or Firm* — MH2 Technology Law Group LLP

(57) ABSTRACT
An electric circuitry for baseline extraction in a photon counting system includes an input signal integrity detector to determine an integrity of an input signal for baseline extraction, a sampling circuit to sample the input signal during a sampling time, and to provide a sampled version of the input signal, a signal processing circuit to process the sampled version of the input signal, and a signal processing controller to control the signal processing circuit. The input signal integrity detector is configured to determine the integrity of the input signal for baseline extraction by evaluating the input signal or the sampled version of the input signal. The signal processing controller is configured to control the signal processing circuit so that the sampled version of the
(Continued)

input signal is processed, when the integrity of the input signal for baseline extraction is determined by the input signal integrity detector at least during the sampling time.

15 Claims, 8 Drawing Sheets

(51) Int. Cl.

| | |
|---|---|
| *G01T 1/178* | (2006.01) |
| *G01T 1/24* | (2006.01) |
| *G01T 1/29* | (2006.01) |

(58) Field of Classification Search
CPC ... A61B 6/4241; A61B 6/4258; A61B 6/4266; A61B 6/4275; A61B 6/4429; A61B 6/4435; A61B 6/4441; A61B 6/4447; A61B 6/482; A61N 6/4283; G01T 1/24; G01T 1/242; G01T 1/243; G01T 1/244; G01T 1/247; G01T 1/29; G01T 1/2914; G01T 1/2921; G01T 1/2928
USPC ................. 378/5, 19, 98.8, 98.9; 250/370.09
See application file for complete search history.

(56) References Cited

U.S. PATENT DOCUMENTS

| | | | | |
|---|---|---|---|---|
| 6,609,075 | B1 | 8/2003 | Warburton et al. | |
| 7,149,278 | B2 * | 12/2006 | Arenson | G01T 1/1647 |
| | | | | 378/19 |
| 7,209,536 | B2 * | 4/2007 | Walter | A61B 6/4042 |
| | | | | 378/5 |
| 7,369,642 | B2 * | 5/2008 | Eilbert | G01T 1/2928 |
| | | | | 378/57 |
| 7,453,987 | B1 * | 11/2008 | Richardson | G01V 5/234 |
| | | | | 378/57 |
| 7,592,596 | B2 * | 9/2009 | Klein | G01T 1/171 |
| | | | | 250/370.06 |
| 7,966,155 | B2 * | 6/2011 | Warburton | G01T 1/17 |
| | | | | 702/190 |
| 8,378,310 | B2 * | 2/2013 | Bornefalk | G06T 11/005 |
| | | | | 250/370.01 |
| 8,384,038 | B2 | 2/2013 | Guo et al. | |
| 8,816,290 | B2 * | 8/2014 | Hamlin | G01T 1/17 |
| | | | | 250/370.08 |
| 8,981,307 | B2 * | 3/2015 | Ohi | A61B 6/4258 |
| | | | | 250/369 |
| 9,000,385 | B2 * | 4/2015 | Dror | G01T 1/171 |
| | | | | 250/370.06 |
| 9,029,793 | B2 * | 5/2015 | Spartiotis | H04N 23/30 |
| | | | | 378/21 |
| 9,121,955 | B2 * | 9/2015 | Schmitt | G01T 1/247 |
| 9,176,238 | B2 | 11/2015 | Herrmann et al. | |
| 9,268,035 | B2 * | 2/2016 | Herrmann | G01T 1/171 |
| 9,301,378 | B2 * | 3/2016 | Steadman Booker | H05G 1/26 |
| 9,351,701 | B2 * | 5/2016 | Yamakawa | A61B 6/4241 |
| 9,354,331 | B2 * | 5/2016 | Sagoh | A61B 6/4241 |
| 9,354,351 | B2 * | 5/2016 | Jorion | G01T 1/171 |
| 9,417,339 | B2 * | 8/2016 | Spahn | A61B 6/4241 |
| 9,444,344 | B2 * | 9/2016 | Kim | G01T 1/247 |
| 9,504,438 | B2 * | 11/2016 | Proksa | H01J 35/10 |
| 9,517,045 | B2 * | 12/2016 | Kang | A61B 6/4241 |
| 9,595,101 | B2 * | 3/2017 | Kato | A61B 6/4241 |
| 9,668,706 | B2 * | 6/2017 | Kim | A61B 6/4283 |
| 9,678,220 | B2 * | 6/2017 | Herrmann | G01T 1/208 |
| 9,700,268 | B2 * | 7/2017 | Kang | A61B 6/4241 |
| 9,730,665 | B2 * | 8/2017 | Choi | A61B 6/4241 |
| 9,759,822 | B2 * | 9/2017 | Daerr | G01T 1/17 |
| 9,907,528 | B2 * | 3/2018 | Yi | A61B 6/4241 |
| 9,964,650 | B2 * | 5/2018 | Cho | G01T 1/247 |
| 9,986,957 | B2 * | 6/2018 | Cho | A61B 6/032 |
| 10,034,652 | B2 * | 7/2018 | Cho | A61B 6/4241 |
| 10,052,077 | B2 * | 8/2018 | Jung | A61B 6/4241 |
| 10,061,038 | B2 * | 8/2018 | Cao | G01T 7/00 |
| 10,080,533 | B2 * | 9/2018 | Roessl | A61B 6/4241 |
| 10,098,595 | B2 * | 10/2018 | Surendranath | A61B 6/4208 |
| 10,117,628 | B2 * | 11/2018 | Tamura | A61B 6/032 |
| 10,149,655 | B2 * | 12/2018 | Kato | A61B 6/4241 |
| 10,162,066 | B2 * | 12/2018 | Fu | G01T 1/247 |
| 10,185,044 | B2 * | 1/2019 | Noshi | A61B 6/482 |
| 10,281,592 | B2 * | 5/2019 | Kawata | A61B 6/032 |
| 10,416,324 | B2 * | 9/2019 | Cao | G01T 1/247 |
| 10,426,415 | B2 * | 10/2019 | Spahn | A61B 6/4241 |
| 10,433,811 | B2 * | 10/2019 | Jacob | A61B 6/4233 |
| 10,441,238 | B2 * | 10/2019 | Terui | G06T 11/005 |
| 10,463,329 | B2 * | 11/2019 | Nagai | A61B 6/4042 |
| 10,524,745 | B2 * | 1/2020 | Tamura | A61B 6/5205 |
| 10,677,942 | B2 * | 6/2020 | Cao | G01T 1/247 |
| 10,705,031 | B2 * | 7/2020 | Cao | G21K 7/00 |
| 10,713,822 | B2 * | 7/2020 | Lee | G01T 1/2985 |
| 10,948,613 | B2 * | 3/2021 | Cao | G01T 1/2928 |
| 10,980,506 | B2 * | 4/2021 | Roessl | G01N 23/046 |
| 10,996,351 | B2 * | 5/2021 | Steadman Booker | G01T 1/247 |
| 11,016,040 | B2 * | 5/2021 | Yamakawa | G01N 23/083 |
| 11,029,425 | B2 * | 6/2021 | Steadman Booker | G01T 1/247 |
| 11,041,968 | B2 * | 6/2021 | Danielsson | G01T 1/242 |
| 11,045,153 | B2 * | 6/2021 | Takahashi | A61B 6/4241 |
| 11,067,440 | B2 * | 7/2021 | Viswanath | G01J 1/44 |
| 11,099,279 | B2 * | 8/2021 | Steadman Booker | G01T 1/17 |
| 11,166,683 | B2 * | 11/2021 | Carbonne Dit Leychert Garenne | A61B 6/4241 |
| 11,229,413 | B1 * | 1/2022 | Lai | A61B 6/032 |
| 11,255,981 | B2 * | 2/2022 | Sjölin | G01T 1/247 |
| 11,635,531 | B2 * | 4/2023 | Zhao | G01T 1/17 |
| | | | | 250/369 |
| 12,196,897 | B2 * | 1/2025 | Taguchi | G01T 1/247 |
| 2006/0015290 | A1 | 1/2006 | Warburton et al. | |
| 2014/0254749 | A1 | 9/2014 | Steadman Booker et al. | |
| 2019/0170880 | A1 | 6/2019 | Booket et al. | |
| 2019/0201024 | A1 | 7/2019 | Shelton, IV et al. | |

OTHER PUBLICATIONS

User Manual: "DPP-ZLEplus Digital Pulse Processing for Zero Length Encoding" UM2764. Rev. 0, Italy, CAEN, Jun. 17, 2014.

Van Ouytsel, K. (Authorized Officer), International Search Report and Written Opinion dated Mar. 30, 2022, PCT Application No. PCT/EP2021/083967, 9 pages.

German Office Action issued in German Patent Application No. 102020132798.6 dated Jul. 30, 2021, 6 pages.

J-D Leroux et al: "Time Determination of BGO-APD Detectors by Digital Signal Processing for Positron Emission Tomography" IEEE Transactions on Nuclear Science, IEEE, USA, vol. 56, No. 5, Oct. 1, 2009, pp. 2600-2606, XP011278010.

Linares-Barranco, B et al.: "A Precise 90 Quadrature OTA-C Oscillator Tunable in the 50-130-MHz Range" IEEE Trans. Circuits Syst. I Reg. Papers, vol. 51, No. 4, pp. 649-664, Apr. 2004.

* cited by examiner

ELECTRIC CIRCUITRY FOR BASELINE EXTRACTION IN A PHOTON COUNTING SYSTEM

CROSS-REFERENCE TO RELATED APPLICATIONS

The present application is the national stage entry of International Patent Application No. PCT/EP2021/083967, filed on Dec. 2, 2021, and published as WO 2022/122545 A1 on Jun. 16, 2022, which claims priority to German Application No. 10 2020 132 798.6, filed on Dec. 9, 2020, the disclosures of all of which are incorporated by reference herein in their entireties.

TECHNICAL FIELD

The disclosure relates to an electric circuitry for baseline extraction in a photon counting system, such as a multi-energy spectral CT (computed tomography). The disclosure further relates to a photon counting circuitry, and a device for medical diagnostics.

BACKGROUND

In a conventional X-ray sensor, an indirect detection principle is used to detect a photon which passes easily through soft tissues of the body of a patient. Indirect detectors comprise a scintillator to convert X-rays to visible light which is captured by a photodetector or photodiode to provide an electrical signal in response to the X-rays impinging on the material of the scintillator.

In a photon counting system, a direct detection principle is used, which allows to detect and count single photon events in order to obtain intensity and spectral information. Whereas in a classical image or X-ray sensor system only the total input intensity is measured, in a photon counting system the photon energy can also be extracted because photons are detected individually.

FIG. 1 shows a block diagram of a photon counting circuitry 2, comprising a front-end electronic circuitry 10, a photon detector 20, and an energy discriminator 30. The photon detector 20 generates a transient current pulse Ipulse caused by a photon impinging a photosensitive area 21 of the photon detector 20. Detection of single photons is enabled by a special sensor material of the photosensitive area 21 (typically CdTe or CdZnTe for X-ray conversion), which converts photons into current pulses Ipulse. These current pulses Ipulse are received at an input node I10 of the front-end electronic circuitry 10 and are converted to voltage pulses Vpulse generated at an output node O10 of the front-end electronic circuitry 10.

The height of the output voltage peak is proportional to the photon energy, thus containing spectral information. Digitization of the spectral information (output pulse height) can be performed using the energy discriminator 30, for example a flash ADC, which comprises several comparators with different thresholds $Vth1, \ldots, VthN-1, VthN$. The output signals of the comparators are then individually counted in order to obtain a spectral distribution.

The static output voltage of the front-end electronic circuitry 10 in the absence of current pulses at its input is called baseline signal and serves as a reference for the discrimination of the pulse heights by the comparators of the energy discriminator 30. As a consequence, changes of the baseline have a direct impact on the observed count rate and pulse energy measurement.

In the case of a DC path from the input node I10 of the front-end electronic circuitry 10 to the output of the photon detector 20, leakage current can directly affect baseline stability, so that either the energy discriminator 30 must be dynamically referenced to the changing baseline or the baseline itself must be stabilized in a feedback loop (baseline restoration). In both approaches accurate extraction of the baseline in the presence of pulse activity at the output node O10 of the front-end electronic circuitry 10 is a major challenge.

There is a need to provide an electric circuitry for baseline extraction in a photon counting system which enables baseline extraction with high accuracy and high tracking speed.

Furthermore, there is a desire to provide a photon counting circuitry having high performance regarding counting rates and energy resolution.

Moreover, there is a desire to provide a device for medical diagnostics capable of operating at very high count rates.

SUMMARY

An electric circuitry which allows baseline extraction in a photon counting system with high accuracy is specified herein.

The electric circuitry for baseline extraction comprises an input terminal to apply an input signal, an input signal integrity detector to determine an integrity of the input signal for baseline extraction, and a sampling circuit to sample the input signal during a sampling time, and to provide a sampled version of the input signal. The electric circuitry for baseline extraction further comprises a signal processing circuit to process the sampled version of the input signal, and a signal processing controller to control the signal processing circuit.

The input signal integrity detector is configured to determine the integrity of the input signal for baseline extraction by evaluating the input signal or the sampled version of the input signal. The signal processing controller is configured to control the signal processing circuit so that the sampled version of the input signal is processed when the integrity of the input signal for baseline extraction is determined by the input signal integrity detector at least during the sampling time.

The proposed approach of the electric circuitry for baseline extraction enables baseline extraction with high accuracy and high tracking speed. At the same time, sensitivity to pulse undershoot and channel crosstalk is minimized. In particular, both high precision in the low flux regime and baseline tracking stability in pile up can be achieved.

The basic structure of the electric circuitry for baseline extraction in a photon counting system is described below.

According to the proposed approach of the electric circuitry for baseline extraction, the input signal integrity detector comprises a range checking circuit. The range checking circuit is configured to provide an error flag signal, when the range checking circuit detects that a level of the input signal or a level of the sampled version of the input signal is out of a monitoring range.

The input terminal of the electric circuitry for baseline extraction may be coupled to the output of a front-end electronic circuit of a photon counting system. The output of the error flag signal by the input signal integrity detector indicates pulse activity of the input signal caused by a photon that hits the photon sensitive area of a photon detector of the photon counting system. The electric circuitry for baseline extraction enables to provide a continuous time range check, when the range checking circuit monitors and evaluates the complete analogue course of the input signal, and to provide a discrete time range check, when the range checking circuit monitors and evaluates the sampled version of the input signal.

According to an embodiment of the electric circuitry for baseline extraction, the electric circuitry comprises a trigger controller having an input side to receive a clock signal and a retrigger signal, and having an output side to provide a start signal and a stop signal. The trigger controller is configured to provide the start signal when the trigger controller receives the clock signal or the retrigger signal at the input side. The trigger controller is further configured to provide the stop signal time-delayed with respect to the start signal.

The proposed configuration enables the baseline sampling times to be defined either by the clock signal or the retrigger signal which is an internally generated clocking event.

According to a possible embodiment of the electric circuitry for baseline extraction in a photon counting system, the signal processing controller has an input side to receive the start signal and the stop signal and the error flag signal. The signal processing controller has an output side to provide a signal processing control signal to control the signal processing circuit when the signal processing controller receives no error flag signal between the application of the start signal and the application of the stop signal at the input side of the signal processing controller. The signal processing circuit is configured to process the sampled version of the input signal, when the signal processing circuit receives the signal processing control signal.

According to an embodiment of the electric circuitry for baseline extraction in a photon counting system, the signal processing controller is configured to provide the retrigger signal at an output side of the signal processing controller to retrigger the trigger controller for generating the start signal and the time-delayed stop signal, when the signal processing controller receives the error flag signal between the application of the start signal and the application of the stop signal at the input side of the signal processing controller.

According to a possible embodiment of the electric circuitry for baseline extraction in a photon counting system, the input signal integrity detector comprises a range controller being configured to adjust the monitoring range. The range controller is configured to adjust the monitoring range in dependence on a frequency with which the retrigger signal is generated by the signal processing controller.

This configuration allows to dynamically adjust the monitoring range of the range checking circuit to optimize precision in the low flux region and allow baseline tracking in pile up. In conclusion, the capability of the electric circuitry for baseline extraction to provide an adaptive monitoring range for the range checking circuit finds the best accuracy for the specific input flux condition.

The range checking circuit has a signal delay time between receiving the input signal or the sampled version of the input signal, and providing the error flag signal. According to a possible embodiment of the electric circuitry for baseline extraction in a photon counting system, the trigger controller is configured such that a time between the generation of the start signal and the stop signal is larger than a sum of the signal delay time of the range checking circuit and the sampling time.

The input signal at the input side of the sampling circuit must be free of any pulse activity throughout the whole sampling period to determine the baseline signal by the signal processing circuit. Consequently, it is required to monitor the input signal or the sampled version of the input signal with regard to being outside the monitoring range throughout the whole sampling period. If it is determined that the level of the input signal or the level of the sampled version of the input signal is within the monitoring range, then the input signal integrity detector determines/detects the integrity of the input signal is sufficient/suited for baseline extraction. As the range checking circuit typically exhibits some signal delay, the total required monitoring period is larger than a sum of the signal delay time of the range checking circuit and the sampling time.

According to an alternative embodiment of the electric circuitry for baseline extraction in a photon counting system, the signal processing controller has an input side to receive the error flag signal. The signal processing controller has an output side to provide a signal processing control signal to control the signal processing circuit, when the signal processing controller receives no error flag signal. The signal processing circuit is configured to process the sampled version of the input signal, when the signal processing circuit receives the signal processing control signal.

According to the alternative embodiment of the electric circuitry for baseline extraction in a photon counting system, the signal processing controller is configured to provide a retrigger signal at the output side of the signal processing controller, when the signal processing controller receives the error flag signal. The input signal integrity detector comprises a range controller being configured to adjust the monitoring range. The range controller is configured to adjust the monitoring range in dependence on a frequency with which the retrigger signal is generated by the signal processing controller.

The range controller allows to dynamically adjust the monitoring range of the range checking circuit to optimize precision in the low flux region and allow baseline tracking in pile up.

According to a possible embodiment of the electric circuitry for baseline extraction in a photon counting system, the range checking circuit comprises a first sub-circuit being configured to provide the error flag signal, when the first sub-circuit detects that a level of the input signal is out of a first threshold of the monitoring range. Furthermore, the range checking circuit comprises a second sub-circuit being configured to provide the error flag signal, when the second sub-circuit detects that a level of the sampled version of the input signal is out of a second threshold of the monitoring range.

This configuration allows a combination of a continuous time range check and a discrete time range check. Assuming that input signal pulses caused by a photon that hits a photon detector result in input signal peaks below the baseline, the first and second threshold may be chosen so that the continuous time range check is performed on the pulse side of the input signal, for example the side of the input signal below the baseline, and the discrete time range check is performed on the non-pulse side, for example the side of the input signal above the baseline. This allows to reduce any distortions in the determination of the baseline during the baseline extraction.

According to an embodiment of the electric circuitry for baseline extraction in a photon counting system, the electric circuitry comprises a sample controller having an input side to receive the start signal or a clock signal, and having an output side to provide a sampling control signal to control the sampling circuit for sampling the input signal in response to the start signal or the clock signal.

This configuration enables to select samples of the input signal for determining the integrity of these samples for the baseline extraction. The start or the clock signal may be provided and applied to the sample controller at regularly repeating intervals so that samples of the input signal are taken at regular time intervals.

According to a further embodiment of the electric circuitry for baseline extraction in a photon counting system, the signal processing circuit is configured to generate an output signal based on averaging of an amount of sampled versions of the input signal, and/or on weighted signal processing of the sampled version of the input signal. In particular, the weighted signal processing is performed by different weightings in dependence on different monitoring ranges.

The proposed configuration of the electric circuitry for baseline extraction thus allows to limit the impact of specific samples with high error by averaging over a specific amount of samples, where different weightings for different check/monitoring ranges can be used.

An embodiment of a photon counting circuitry which allows to detect a large number of photons impinging on a photon detector is specified herein.

The photon counting circuitry comprises the electric circuitry for baseline extraction, as described above. The photon counting circuitry further comprises a photon detector having a photon sensitive area. The photon detector is configured to generate a current signal in dependence on an impact of a photon on the photon sensitive area. The photon counting circuitry comprises a front-end electronic circuitry to receive the current signal and to provide a voltage signal in response to the current signal. Furthermore, the photon counting circuitry comprises an energy discriminator that is connected to the front-end electronic circuitry.

The energy discriminator is configured to generate a digital signal in dependence on a comparison of a level of the voltage signal with at least one threshold value. The energy discriminator is configured to adjust the at least one threshold value in dependence on an output signal provided by the electric circuitry for baseline extraction. Thus, comparator thresholds of the energy discriminator are referred to the extracted baseline.

Another embodiment of a photon counting circuitry, which also allows the detection of a large number of photons impinging on a photon detector, is specified herein.

The photon counting circuitry comprises a photon detector having a photon sensitive area. The photon detector is configured to generate a current signal in dependence on an impact of a photon on the photon sensitive area. The photon counting circuitry further comprises a front-end electronic circuitry to receive the current signal and to provide a voltage signal in response to the current signal. The photon counting circuitry further comprises an energy discriminator being connected to the output side of the front-end electronic circuitry.

The energy discriminator is configured to generate a digital signal in dependence on a comparison of a level of the voltage signal with at least one threshold value. The photon counting circuitry further comprises a baseline restoration circuit being connected between the input and output side of the front-end electronic circuitry. The baseline restoration circuit comprises the electric circuitry for baseline extraction, as described above.

The proposed configuration of the photon counting circuitry allows to compensate leakage current from the photon detector.

A device for medical diagnostics using the principle of photon counting is specified herein.

The device comprises the photon counting circuitry according to one of the embodiments described above. The device for medical diagnostics may be configured as an X-ray apparatus or a computed tomography scanner.

Additional features and advantages of the electric circuitry for baseline extraction a photon counting system are set forth in the detailed description that follows. It is to be understood that both the foregoing general description and the following detailed description are merely exemplary, and are intended to provide an overview or framework for understanding the nature and character of the claims.

BRIEF DESCRIPTION OF THE DRAWINGS

The accompanying drawings are included to provide further understanding, and are incorporated in, and constitute a part of, the specification. As such, the disclosure will be more fully understood from the following detailed description, taken in conjunction with the accompanying figures in which.

DETAILED DESCRIPTION OF THE EMBODIMENTS

Figure 2:
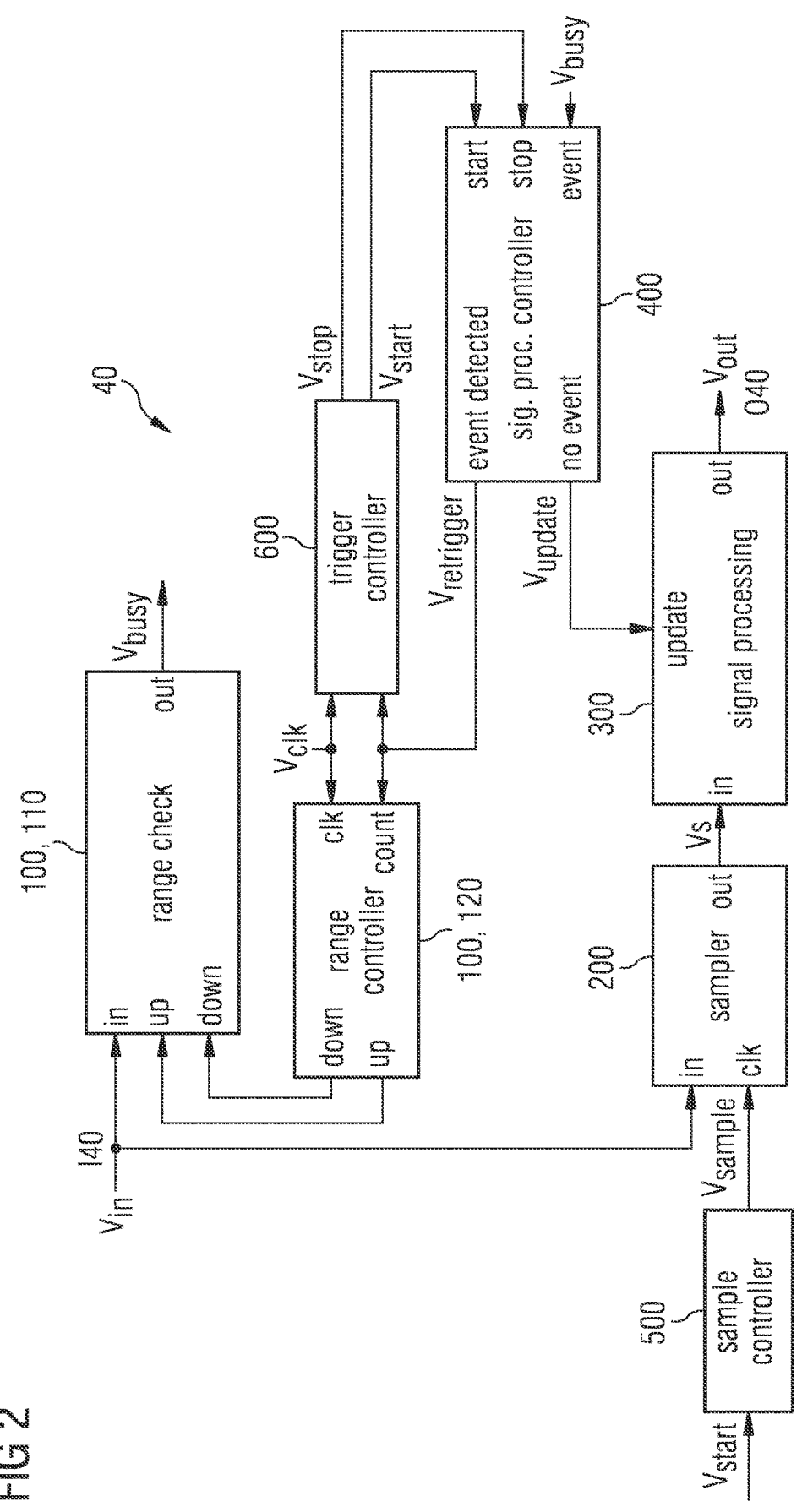
FIG. 2 shows a first embodiment of an electric circuitry for baseline extraction in a photon counting system which enables baseline extraction with high accuracy and high tracking speed, wherein the integrity of an input signal for baseline extraction is detected by evaluating the input signal.
Figure 4:
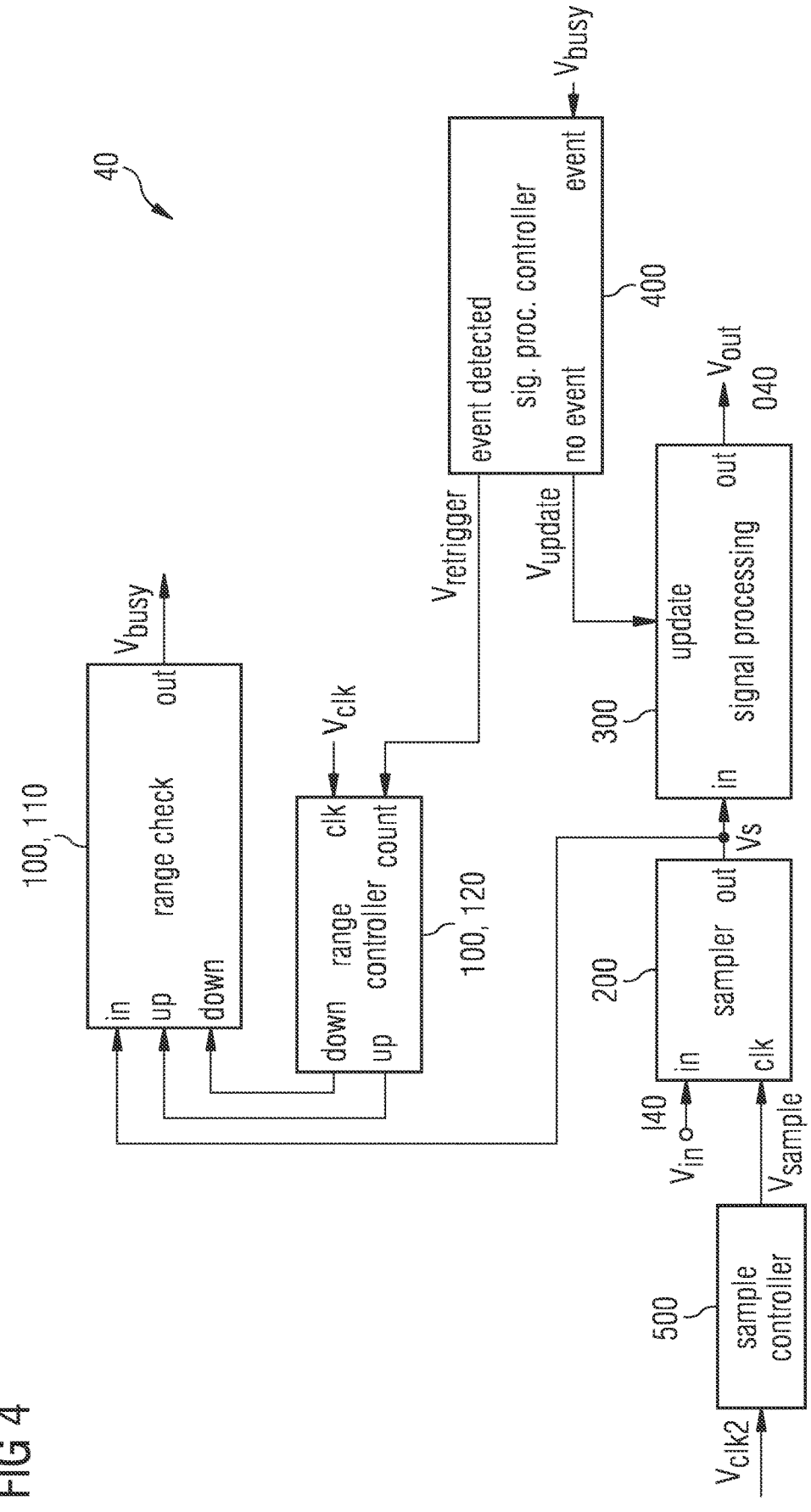
FIG. 4 shows a second embodiment of an electric circuitry for baseline extraction in a photon counting system which enables baseline extraction with high accuracy and high tracking speed, wherein the integrity of an input signal for baseline extraction is detected by evaluating a sampled version of an input signal.

The proposed electric circuitry for baseline extraction in a photon counting system uses a sample-based baseline extraction scheme, as shown in a first embodiment in FIG. 2 and as shown in a second embodiment in FIG. 4. Both of the approaches enable baseline extraction with high accuracy and high tracking speed. Moreover, time sensitivity to pulse undershoot and channel crosstalk can be minimized with the proposed approaches for an electric circuitry for baseline extraction in a photon counting system.

Both embodiments of an electric circuitry for baseline extraction are described in the following with reference to FIGS. 2, 3 and 4. The blocks and the terms used for the blocks reflect the functional description of the baseline restorer circuitry 40 of the first and second embodiments, irrespective of how this functionality is implemented in hardware, for example in one or more IC chips, etc.

Figure 1:
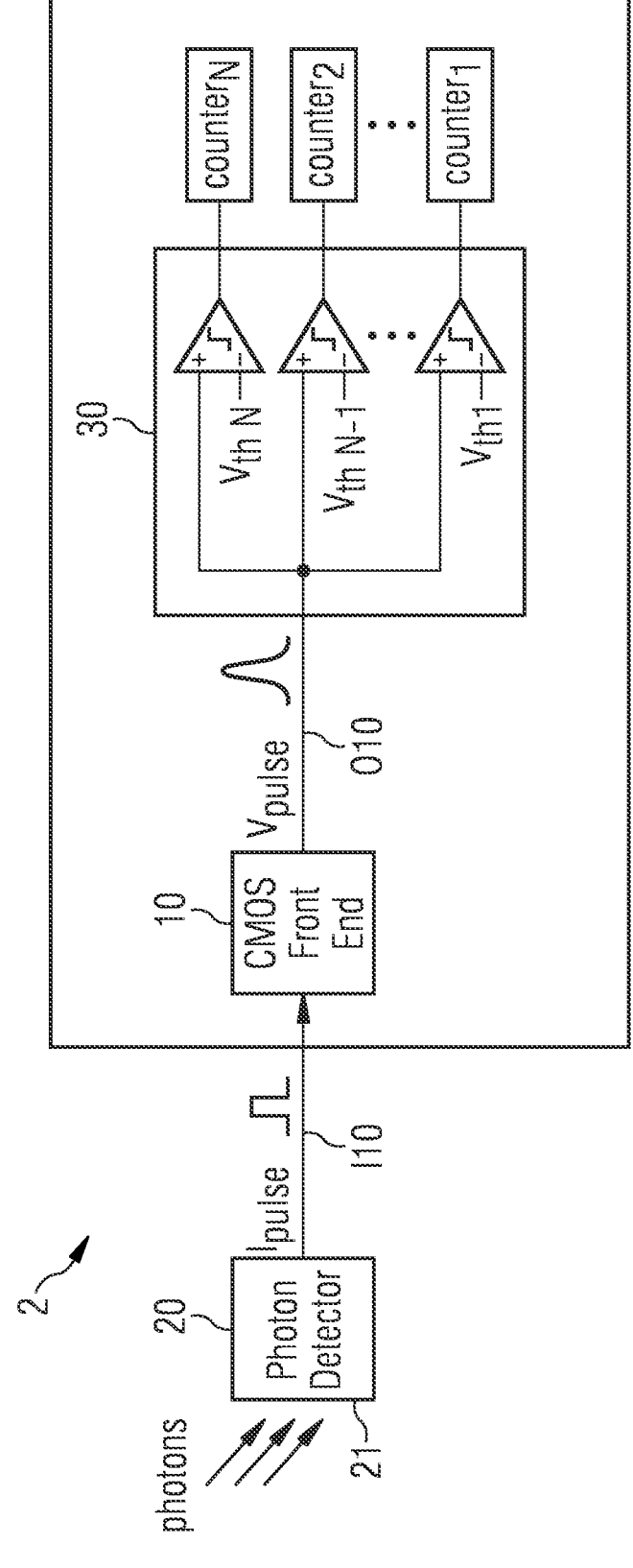
FIG. 1 shows a block diagram of a photon counting circuitry.

Referring to the first embodiment of an electric circuitry 40 for baseline extraction in a photon counting system shown in FIG. 2, the electric circuitry 40 comprises an input terminal 140 to apply an input signal Vin. The input terminal 140 may be coupled to a front-end electronic circuitry 10 of a photon counting system. The front-end electronic circuitry may be coupled to a photon detector 20, as shown in FIG. 1.

The front-end electronic circuitry 10 provides a pulse at the input terminal 140 of the electric circuitry 40 in case a photon hits the radiation-sensitive surface 21 of the photon detector 20. In the absence of pulse activity, the front-end electronic circuitry 10 provides a static front-end output voltage (baseline signal) at the input terminal 140.

As shown in FIG. 2 the electric circuitry 40 for baseline extraction comprises an input signal integrity detector 100 to determine an integrity of the input signal Vin sufficient, i.e. suitable, for baseline extraction. The electric circuitry 40 further comprises a sampling circuit 200 to sample the input signal Vin during a sampling time Tsample, and to provide a sampled version Vs of the input signal Vin. The electric circuitry 40 comprises a signal processing circuit 300 to process the sampled version Vs of the input signal Vin, and a signal processing controller 400 to control the signal processing circuit 300.

The input signal integrity detector 100 is configured to determine the integrity of the input signal Vin to be sufficient for baseline extraction by evaluating the input signal. This allows a time continuous evaluation of the input signal to be suitable for baseline extraction, when no pulse activity has been detected on the input signal. The signal processing controller 400 is configured to control the signal processing circuit 300 so that the sampled version Vs of the input signal Vin is processed when the integrity of the input signal Vin is determined by the input signal integrity detector 100 to be sufficient for baseline extraction at least during the sampling time Tsample, i.e. no pulse activity is present at the input terminal 140.

As further shown in FIG. 2, the input signal integrity detector 100 comprises a range checking circuit 110 being configured to provide an error flag signal Vbusy, when the range checking circuit 110 detects that a level of input signal Vin is out of a monitoring range. The occurrence of the error flag signal Vbusy at the input side of the signal processing controller 400 indicates that pulse activity of the input signal Vin was detected by the input signal integrity detector 100.

The electric circuitry 40 comprises a trigger controller 600 having an input side to receive a clock signal Vclk and a retrigger signal Vretrigger. The clock signal Vclk is generated with a defined period. The retrigger signal is generated only, when the occurrence of a pulse of the input signal is detected by evaluating the input signal Vin. The trigger controller 600 has an output side to provide a start signal Vstart and a stop signal Vstop. In particular, the trigger controller 600 is configured to provide the start signal Vstart, when the trigger controller 600 receives the clock signal Vclk or the retrigger signal Vretrigger at the input side. The trigger controller 600 is further configured to provide the stop signal Vstop time-delayed with respect to the start signal Vstart.

The signal processing controller 400 has an input side to receive the start signal Vstart and the stop signal Vstop and the error flag signal Vbusy. The signal processing controller 400 has an output side to provide a signal processing control signal Vupdate to control the signal processing circuit 300, when the signal processing controller 400 receives no error flag signal Vbusy, for example a low level/zero level of the error flag signal Vbusy, between the application of the start signal Vstart and the application of the stop signal Vstop at the input side of the signal processing controller 400.

The absence of the error flag signal Vbusy at the input side of the signal processing controller 400 indicates that no pulse activity of the input signal Vin was detected by the input signal integrity detector 100 at the input terminal 140. The signal processing circuit 300 is configured to process the sampled version Vs of the input signal, when the signal processing circuit 300 receives the signal processing control signal Vupdate. That means that once a valid, i.e. a pulse-free, sample of the input signal has been acquired, the sample output is transferred to the signal processing chain. The signal processing circuit 300 processes the sampled version Vs of the input signal and outputs an output signal Vout at an output terminal 040 of the electric circuitry 40. The output signal Vout represents the baseline signal estimate or a processed version of it.

The signal processing controller 400 is configured to provide the retrigger signal Vretrigger at the output side of the signal processing controller 400 to retrigger the trigger controller 600 for generating the start signal Vstart and the time-delayed stop signal Vstop, when the signal processing controller 400 receives the error flag signal Vbusy, for example a high level, 1-level, or a pulse of the error flag signal, between the application of the start signal Vstart and the application of the stop signal Vstop at the input side of the signal processing controller 400. That means that the retrigger signal Vretrigger is generated by the signal processing controller 400 when an event of pulse activity indicated by the error flag signal Vbusy is detected by the input signal integrity detector 100.

According to the proposed approach of the electric circuitry 40 for baseline extraction, the baseline sampling times are defined either by the clock signal Vclk or the retrigger signal Vretrigger being configured as a clocking event internally generated by the signal processing controller 400. The clock input may be delayed along the channel chain in order to avoid concurrent switching which can cause supply disturbances.

According to the proposed approach of the electric circuitry 40 for baseline extraction, a bipolar range check is employed by the range checking circuit 110 to determine if pulse activity is present at the input terminal 140 that prevents accurate sampling of the baseline. In particular, if the input signal Vin is beyond an upper and lower threshold of the monitoring range, the range checking circuit 110 will output the error flag signal Vbusy.

It has to be noted that the range checking circuit 110 has a signal delay time Td_check between receiving the input signal Vin, and providing the error flag signal Vbusy at its output side. The trigger controller 600 is configured such that a time between the generation of the start signal Vstart and the stop signal Vstop, i.e. a monitoring time Tmonitor is larger than a sum of the sampling time Tsample and the delay time TD_check.

In order to avoid corrupting the signal processing chain accurate samples are required that should not experience pulse disturbances. Therefore, the sample input must be free of any pulses of the input signal throughout the whole sampling period. As the range checking circuit 110 exhibits some signal delay time Td_check, the total required monitoring period is given as Tmonitor>Tsample+Td_check.

Therefore, a timer must be started upon the generation of the start signal Vstart. This can be realized by a delay block or a clock counter inside the signal processing controller 400 with a delay equal to or larger than the monitoring time Tmonitor. In the case that a range violation is detected during the monitoring time Tmonitor, the last sample is discarded and the sample process is automatically retriggered immediately or synchronously with the next edge of an internal or external clock signal, having a frequency higher than the input clock. Hence, in the case of continuous pulse activity at the output of the front-end electronic circuitry input terminal 140 of the electric circuitry 40, sampling is repeated until an accurate sample is found. The auto retrigger is reset with the next input clock edge.

Referring to FIG. 2, the input signal integrity detector 100 comprises a range controller 120 being configured to adjust the monitoring range. The range controller 120 is configured to adjust the monitoring range in dependence on a frequency with which the retrigger signal Vretrigger is generated by the signal processing controller 400.

According to the proposed approach, the monitoring range used by the range checking circuit 110 can thus dynamically be adjusted by the range controller 120 to optimize precision in the low flux region and allow baseline tracking in pile up. Based on the number of retrigger events per clock period a safe monitoring range used by the range checking circuit 110 can be adjusted by the range controller 120.

In the case that a high number of retrigger events were necessary, this hints at output pulse activity and to maintain a constant rate of accepted samples the monitoring range can be increased at the cost of baseline estimation accuracy. On the other hand, in the case that no retrigger events were required for some number of clock periods, the monitoring range can be narrowed by the range controller 120 to obtain higher accuracy.

As shown in FIG. 2, the electric circuitry 40 comprises a sample controller 500 having an input side to receive the start signal Vstart and having an output side to provide a sampling control signal Vsample to control the sampling circuit 200 for sampling the input signal Vin in response to the start signal Vstart.

In order to limit the impact of specific samples with high error, averaging of a specific amount of samples by the signal processing circuit 300 can be implemented, where different weightings for different check ranges can be used, i.e. samples taken based on a higher monitoring range are weighted less than samples taken based on a narrow monitoring range to reduce error impact.

For this purpose, the signal processing circuit 300 may be configured to generate an output signal Vout at an output terminal O40 representing the baseline signal, wherein the output signal Vout is based on averaging of an amount of sampled versions Vs of the input signal, and/or on weighted signal processing of the sampled version Vs of the input signal. In particular, the signal processing circuit 300 is configured to perform the weighted signal processing by using different weightings in dependence on different monitoring ranges. In the case that a baseline feedback circuit is employed, averaging can be performed by an integrator in the loop.

Figure 3:
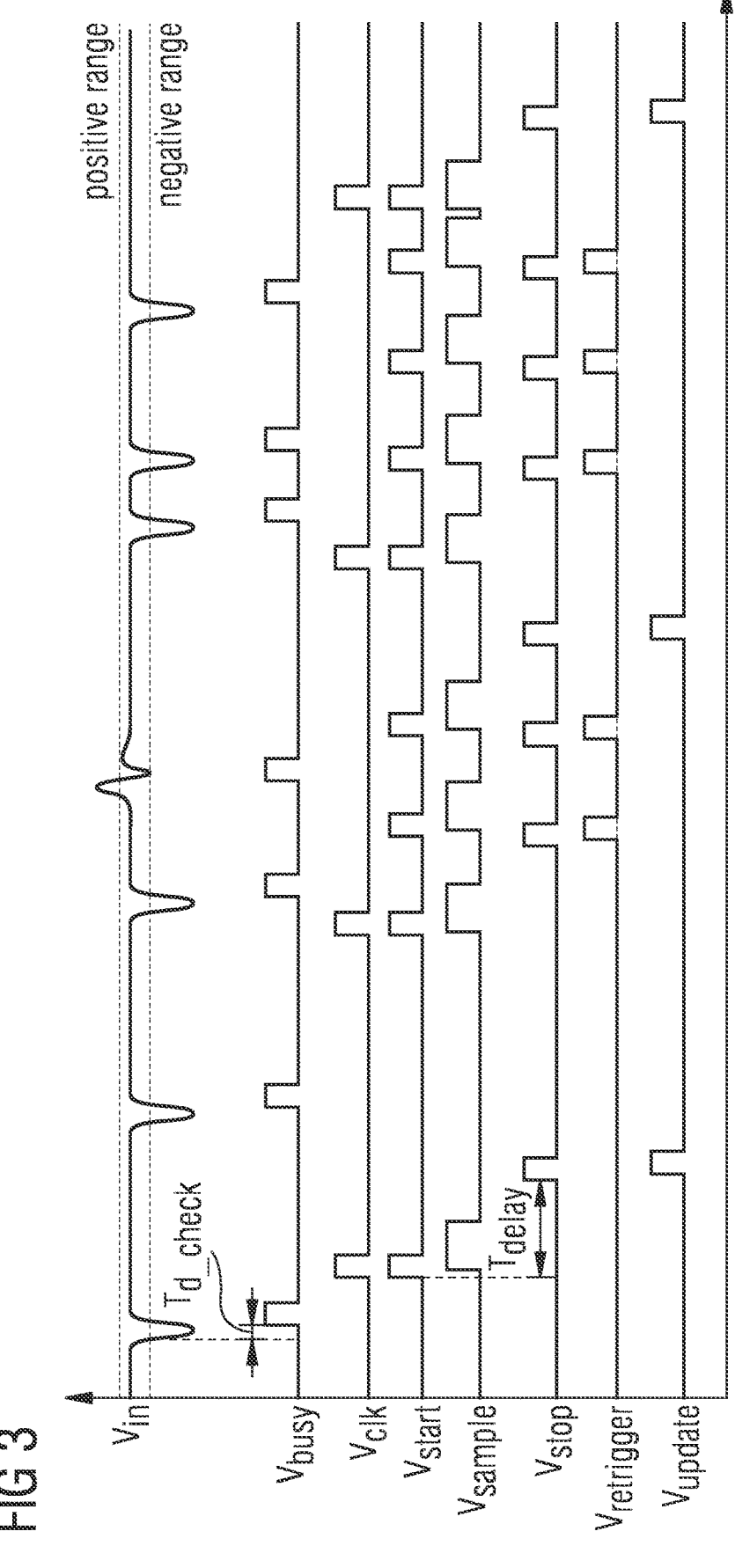
FIG. 3 illustrates the functionality of the electric circuitry for baseline extraction by a baseline extractor timing diagram.

The function of the electric circuitry for baseline extraction in a photon counting system will be explained in the following on the basis of FIG. 3 showing a baseline extractor timing diagram.

The timing diagram shows the course of the input signal Vin and the generation of several control signals of the electric circuitry 40 for baseline extraction. In the case where a pulse activity of the input signal Vin is detected, i.e. when the input signal Vin exceeds the monitoring range marked by the dashed thresholds in FIG. 3, the input signal integrity detector 100 generates the error flag signal Vbusy (with a signal delay time Td_check) at its output side. FIG. 3 shows pulses on the input signal in the negative range ("pulse side") below the baseline, wherein these pulses result from photons that hit a photon detector, and disturbing pulses on the input signal in the positive range ("non-pulse side") above the baseline.

The clock signal Vclk is repeated periodically. After having received a pulse of the clock signal Vclk, a sample trial is triggered by the trigger controller 600 which generates the start signal Vstart and subsequently generates the stop signal Vstop time-delayed to the start signal Vstart. The start signal Vstart further causes the sampling circuit 200 to sample the input signal Vin and to provide the sampled version Vs of the input signal.

In the case that no pulse activity of the input signal Vin is present during the monitoring time between the triggering of the start signal Vstart and the stop signal Vstop by the trigger controller 600, the signal processing controller 400 outputs the signal processing control signal Vupdate. As a consequence of the signal processing control signal, the signal processing circuit 300 processes the sampled version Vs of the input signal for baseline extraction, and outputs the output signal Vout being a representation of the baseline signal.

Referring again to FIG. 3, if pulse activity is present during the monitoring time between the start signal Vstart and the stop signal Vstop, i.e. an error flag signal Vbusy is output by the input signal integrity detector 100/the range checking circuit 110, the retrigger signal Vretrigger is output by the signal processing controller 400 to retrigger another sample trial. That means that the trigger controller 600 again generates the start signal Vstart and the time-delayed stop signal Vstop, and the sampling circuit 200 samples the input signal Vin and provides a sampled version Vs of the input signal Vin at its output side.

In the case the retrigger signal Vretrigger is output by the signal processing controller 400, and a clock pulse Vclk is output shortly afterwards, another sample trail is started, as a result of the reception of the clock signal Vclk by the trigger controller 600. Thus, the trigger controller 600 generates the start signal Vstart and the time-delayed stop signal Vstop in response to the pulse of the clock signal Vclk.

FIG. 4 shows a second embodiment of an electric circuitry 40 for baseline extraction in a photon counting system. The same functional blocks as shown in FIG. 2 are marked with the same reference signs.

The electric circuitry 40 for baseline extraction of the second embodiment comprises the input terminal 140 to apply the input signal Vin, an input signal integrity detector 100 to determine an integrity of the input signal Vin sufficient, i.e. suitable, for baseline extraction, the sampling circuit 200 to sample the input signal Vin during a sampling time Tsample and to provide a sampled version Vs of the input signal Vin, the signal processing circuit 300 to process the sampled version Vs of the input signal Vin, and a signal processing controller 400 to control the signal processing circuit 300.

The input signal integrity detector 100 comprises a range checking circuit 110 to provide the error flag signal Vbusy, and the range controller 120 to adjust the monitoring range. The electric circuitry 40 further comprises the sample controller 500 receiving a clock signal Vclk2. The sample controller 500 provides the sampling control signal Vsample to control the sampling circuit 200 for sampling the input signal Vin in response to the clock signal Vclk2.

In the following, the main differences of the second embodiment of the electric circuitry 40 to the first embodiment of the electric circuitry 40 shown in FIG. 2 are explained.

In contrast to the first embodiment of the electric circuitry 40 for baseline extraction, according to the second embodiment of the electric circuitry 40 shown in FIG. 4, the input signal integrity detector 100 is configured to determine the integrity of the input signal Vin to be sufficient for baseline extraction by evaluating the sampled version Vs of the input signal Vin. This allows a time-discrete evaluation of the input signal to be suitable for baseline extraction, when no pulse activity has been detected on the sampled version of input signal.

The range checking circuit 110 of the input signal integrity detector 100 is configured to provide the error flag signal Vbusy, when the range checking circuit 110 detects that a level of the sampled version Vs of the input signal is out of the monitoring range. The range checking circuit 110 generates the error flag signal Vbusy, for example a high level, 1-level or pulse of the error flag signal, when the range checking circuit 110 detects that the level of the sampled version Vs of the input signal exceeds the threshold values of the monitoring range shown in FIG. 3. The range checking circuit 110 generates no error flag signal Vbusy, for example a low level, or zero level of the error flag signal, when the range checking circuit 110 detects that the level of the sampled version Vs of the input signal is within the threshold values of the monitoring range shown in FIG. 3.

As shown in FIG. 4, the signal processing controller 400 receives at its input side only the error flag signal Vbusy. The signal processing controller 400 generates the signal processing control signal Vupdate to control the signal processing circuit 300 to process the sampled version Vs of the input signal, when the signal processing controller 400 receives no error flag signal Vbusy, for example a low level or zero level of the error flag signal, at its input side.

The signal processing controller 400 is further configured to provide the retrigger signal Vretrigger at the output side of the signal processing controller 400, when the signal processing controller 400 receives the error flag signal Vbusy, for example a high level, 1-level or pulse of the error flag signal, at its input side. The range controller 120 is configured to adjust the monitoring range in dependence on a frequency with which the retrigger signal Vretrigger is generated by the signal processing controller 400.

In conclusion, according to the second embodiment of the electric circuitry 40 for baseline extraction, pulse activity of the input signal Vin is checked not by directly evaluating the input signal Vin but by evaluating the sampled version Vs of the input signal. The second embodiment of the electric circuitry 40, particularly the range checking circuit 110, thus enables a discrete time range check. If pulse activity was present at the input terminal 140 during sampling, the sampled version Vs of the input signal will fall outside the limits of the monitoring range which is checked by the range checking circuit 110 of the input signal integrity detector 100.

Figure 5:
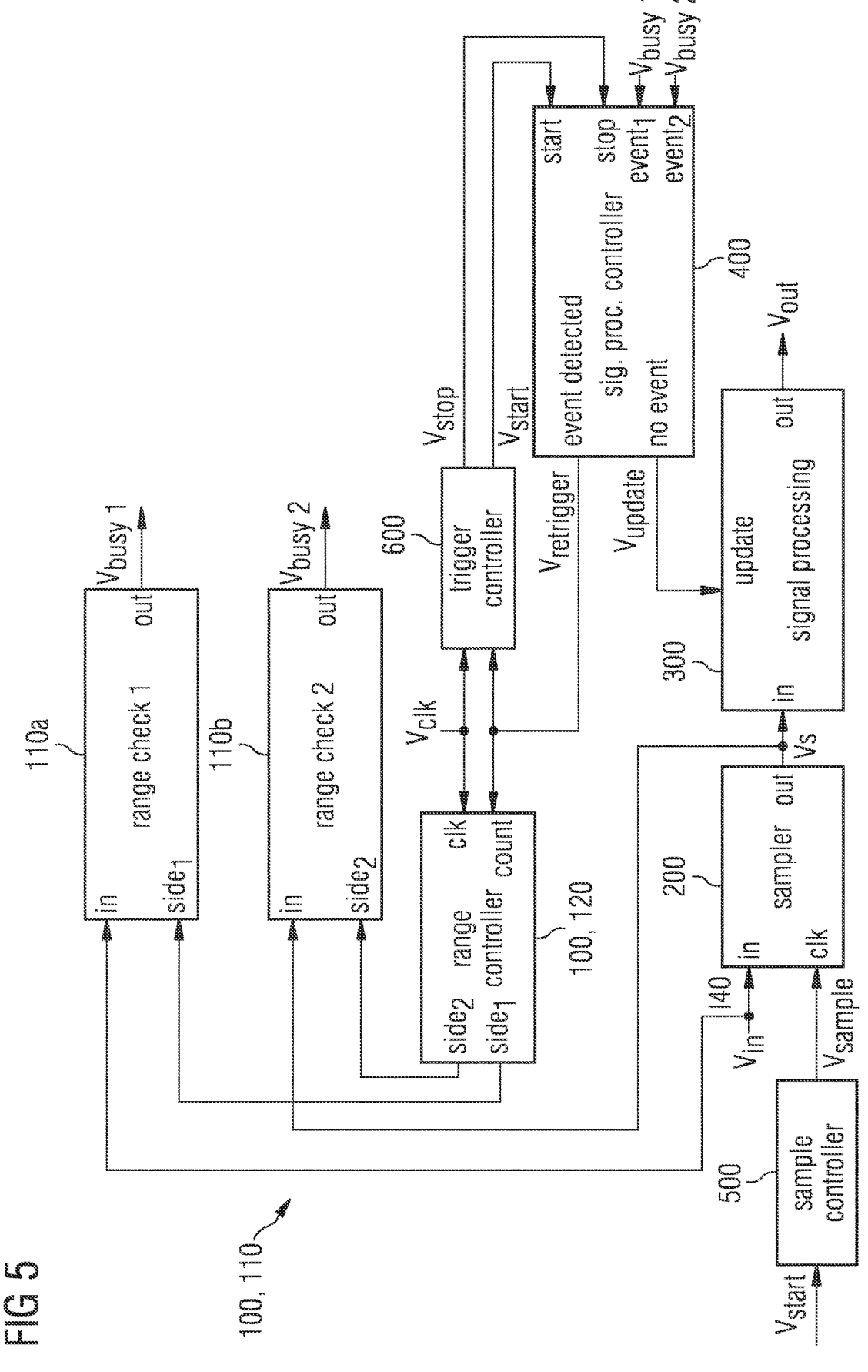
FIG. 5 shows a third embodiment of an electric circuitry for baseline extraction implemented as a combination of the first and second embodiment.

FIG. 5 shows a third embodiment of an electric circuitry 40 for baseline extraction in a photon counting system that is implemented as a combination of the first and second embodiment. The same functional blocks as shown in FIG. 2 and FIG. 4 are marked with the same reference signs. The circuitry 40 comprises an input signal integrity detector 100 including a range checking circuit 110 and the range controller 120. The circuitry 40 further comprises the sampling circuit 200, the signal processing circuit 300, the signal processing controller 400, the sample controller 500, and the trigger controller 600. The operation of the range controller 120, the sampling circuit 200, the signal processing circuit 300, the signal processing controller 400, the sample controller 500, and the trigger controller 600 has been explained in detail with reference to FIGS. 2, 3 and 4.

According to the third embodiment of the electric circuitry the range checking circuit 110 comprises a first sub-circuit 110a being configured to provide the error flag signal Vbusy1, when the first sub-circuit 110a detects that a level of the input signal Vin is out of a first threshold of the monitoring range. The range checking circuit 110 comprises a second sub-circuit 110b being configured to provide the error flag signal Vbusy2, when the second sub-circuit 110b detects that a level of the sampled version Vs of the input signal is out of a second threshold of the monitoring range.

The sub-circuit 110a allows a continuous time comparison and thus a detection of pulse activity for one range/side of the monitoring range, for example the lower range below the baseline, over the time span defined by the start signal Vstart and the stop signal Vstop. The sub-circuit 110b checks the occurrence of pulses for the other range/side of the monitoring range, for example the upper range above the baseline, based on the sampled input signal. Referring to FIG. 5, "side 1" can be the upper or lower range, and "side 2" is the respective other one.

If the coupling of the sub-circuits 110a and 110b to the range controller 120 is chosen such that the continuous time range check is on the pulse side, for example the lower side of the input signal Vin below the baseline shown in FIG. 3, and the discrete time range check is on the non-pulse side, for example the upper side of the input signal Vin above the baseline shown in FIG. 3, distortions in the determination of the baseline can be reduced.

Figure 6:
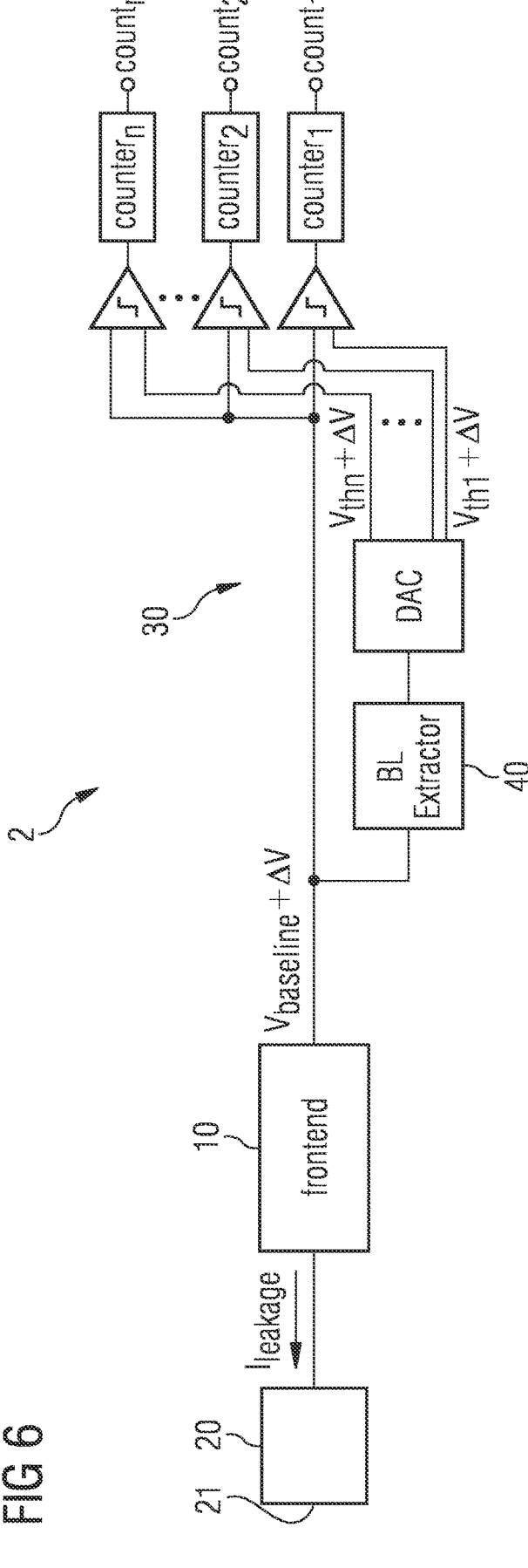
FIG. 6 shows an embodiment of a photon counting circuitry using the electric circuitry for baseline extraction as a baseline drift compensation circuit.
Figure 7:
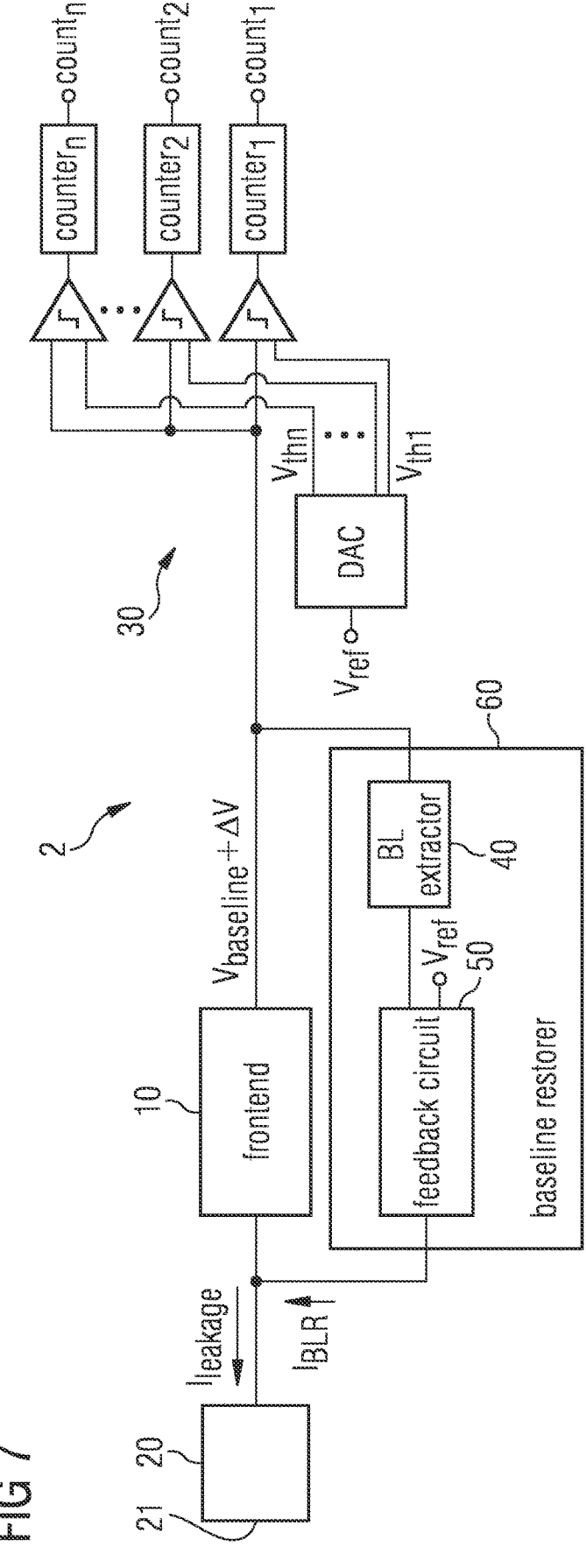
FIG. 7 shows an embodiment of a photon counting circuitry using the electric circuitry for baseline extraction in a baseline restoration circuit.

FIGS. 6 and 7 show a possible application/use of the electric circuitry 40 for baseline extraction in a photon counting circuitry 2.

FIG. 6 shows the use of the electric circuitry 40 for baseline extraction as a baseline drift compensation circuit within a photon counting circuitry 2. The photon counting circuitry 2 comprises a photon detector 20 having a photon sensitive area 21. The photon detector 20 is configured to generate a current signal in dependence on an impact of a photon on the photon sensitive area 21. The photon counting circuitry 2 further comprises a front-end electronic circuitry 10 to receive the current signal from the photon detector 20 and to provide a voltage signal Vbaseline+$\Delta$V in response to the current signal.

The photon counting circuitry 2 comprises an energy discriminator 30 being connected to the front-end electronic circuitry 10. The energy discriminator 30 is configured to generate a digital signal in dependence on a comparison of a level of the voltage signal Vbaseline+$\Delta$V with at least one threshold value Vth1+$\Delta$V . . . , Vthn+$\Delta$V. The photon counting circuitry 2 further comprises the electric circuitry for baseline extraction 40, according to one of the embodiments described above.

The energy discriminator 30 is configured to adjust the at least one threshold value in dependence on the output signal Vout, i.e. the baseline signal, provided by the electric circuitry 40. The baseline is extracted by the proposed approach of the electric circuitry 40 for baseline extraction and supplied as DAC reference so that comparator thresholds of the energy discriminator 30 are referred to the extracted baseline.

A use of the electric circuitry 40 to provide baseline compensation via baseline restoration is depicted in FIG. 7.

Referring to FIG. 7, the photon counting circuitry 2 comprises a photon detector 20 having a photon sensitive area 21. The photon detector 20 is configured to generate a current signal in dependence on an impact of a photon on the photon sensitive area 21. The photon counting circuitry 2 comprises a front-end electronic circuitry 10 to receive the current signal from the photon detector 20 and to provide a voltage signal Vbaseline+ΔV in response to the current signal. The photon counting circuitry 2 comprises an energy discriminator 30 being connected to the front-end electronic circuitry 10. The energy discriminator 30 is configured to generate a digital signal in dependence on a comparison of a level of the voltage signal Vbaseline+ΔV with at least one threshold value Vth1, . . . , Vthn.

The photon counting circuitry 2 comprises a baseline restoration circuit 60 being connected between the input and output side of the front-end electronic circuitry 10. The baseline restoration circuit 60 comprises the proposed approach of the electric circuitry 40 for baseline extraction, according to one of the embodiments, as described above. The difference between the extracted baseline and the reference is applied to a feedback circuit 50 of the baseline restoration circuit 60 and amplified with high gain, or integrated to compensate leakage current from the photon detector 20.

The proposed approach of the electric circuitry 40 for baseline extraction may be used for various photon counting applications, especially those which require low noise intensity measurements and possibly also spectral information. This includes medical imaging, spectroscopy, security scanners, computed tomography, etc.

Figure 8:
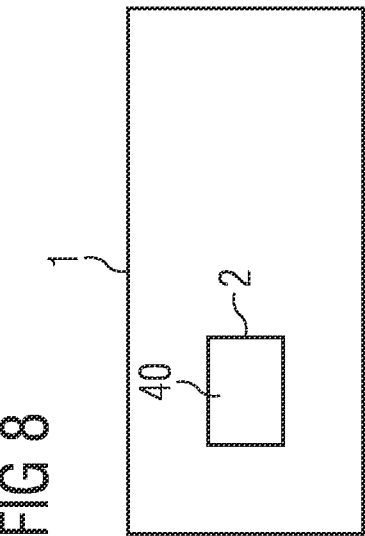
FIG. 8 shows an embodiment of a device for medical diagnostics based on a photon counting principle.

FIG. 8 shows an example of an application where a photon counting circuitry 2 equipped with an electric circuitry 40 for baseline extraction is provided in a device 1 for medical diagnostics. The device 1 may be configured, for example, as an X-ray apparatus or a computed tomography scanner.

The embodiments of the electric circuitry for baseline extraction in a photon counting system disclosed herein have been discussed for the purpose of familiarizing the reader with novel aspects of the design of the electric circuitry for baseline extraction. Although preferred embodiments have been shown and described, many changes, modifications, equivalents and substitutions of the disclosed concepts may be made by one having skill in the art without unnecessarily departing from the scope of the claims.

In particular, the design of the electric circuitry for baseline extraction in a photon counting system is not limited to the disclosed embodiments, and gives examples of many alternatives as possible for the features included in the embodiments discussed. However, it is intended that any modifications, equivalents and substitutions of the disclosed concepts be included within the scope of the claims which are appended hereto.

Features recited in separate dependent claims may be advantageously combined. Moreover, reference signs used in the claims are not limited to be construed as limiting the scope of the claims.

Furthermore, as used herein, the term "comprising" does not exclude other elements. In addition, as used herein, the article "a" is intended to include one or more than one component or element, and is not limited to be construed as meaning only one.

The invention claimed is:

1. An electric circuitry for a baseline extraction in a photon counting system, comprising:
   an input terminal to apply an input signal,
   an input signal integrity detector to determine an integrity of the input signal for the baseline extraction,
   a sampling circuit to sample the input signal during a sampling time, and to provide a sampled version of the input signal,
   a signal processing circuit to process the sampled version of the input signal, and
   a signal processing controller to control the signal processing circuit,
   wherein the input signal integrity detector is configured to determine the integrity of the input signal for the baseline extraction by evaluating the input signal or the sampled version of the input signal, and
   wherein the signal processing controller is configured to control the signal processing circuit so that the sampled version of the input signal is processed, when the integrity of the input signal for the baseline extraction is determined by the input signal integrity detector at least during the sampling time.

2. The electric circuitry of claim 1,
   wherein the input signal integrity detector comprises a range checking circuit, and
   wherein the range checking circuit is configured to provide an error flag signal, when the range checking circuit detects that a level of the input signal or a level of the sampled version of the input signal is out of a monitoring range.

3. The electric circuitry of claim 2, further comprising:
   a trigger controller having an input side to receive a clock signal and a retrigger signal, and having an output side to provide a start signal and a stop signal,
   wherein the trigger controller is configured to provide the start signal, when the trigger controller receives the clock signal or the retrigger signal at the input side, and
   wherein the trigger controller is configured to provide the stop signal time-delayed with respect to the start signal.

4. The electric circuitry of claim 3,
   wherein the signal processing controller has an input side to receive the start signal, the stop signal, and the error flag signal,
   wherein the signal processing controller has an output side to provide a signal processing control signal to control the signal processing circuit, when the signal processing controller receives no error flag signal between an application of the start signal and an application of the stop signal at the input side of the signal processing controller, and
   wherein the signal processing circuit is configured to process the sampled version of the input signal, when the signal processing circuit receives the signal processing control signal provided by signal processing controller.

5. The electric circuitry of claim 4, wherein the signal processing controller is configured to provide the retrigger signal at the output side of the signal processing controller to retrigger the trigger controller for generating the start signal and the time-delayed stop signal, when the signal processing controller receives the error flag signal between the application of the start signal and the application of the stop signal at the input side of the signal processing controller.

6. The electric circuitry of claim 5, wherein the input signal integrity detector comprises a range controller being configured to adjust the monitoring range, and wherein the range controller is configured to adjust the monitoring range in dependence on a frequency with which the retrigger signal is generated by the signal processing controller.

7. The electric circuitry of claim 3, wherein the range checking circuit has a signal delay time between receiving the input signal or the sampled version of the input signal and providing the error flag signal, and wherein the trigger controller is configured such that a time between a generation of the start signal and a generation of the stop signal is larger than a sum of the signal delay time and the sampling time.

8. The electric circuitry of claim 3, further comprising:

a sample controller having an input side to receive the start signal or a second clock signal, and having an output side to provide a sampling control signal to control the sampling circuit for sampling the input signal in response to the start signal or the second clock signal.

9. The electric circuitry of claim 2, wherein the signal processing controller has an input side to receive the error flag signal provided by the range checking circuit, wherein the signal processing controller has an output side to provide a signal processing control signal to control the signal processing circuit, when the signal processing controller receives no error flag signal, and wherein the signal processing circuit is configured to process the sampled version of the input signal, when the signal processing circuit receives the signal processing control signal provided by the signal processing controller.

10. The electric circuitry of claim 2, wherein the signal processing controller is configured to provide a retrigger signal at an output side of the signal processing controller, when the signal processing controller receives the error flag signal provided by the range checking circuit, wherein the input signal integrity detector comprises a range controller being configured to adjust the monitoring range, and wherein the range controller is configured to adjust the monitoring range in dependence on a frequency with which the retrigger signal is generated by the signal processing controller.

11. The electric circuitry of claim 2, wherein the range checking circuit comprises a first sub-circuit being configured to provide the error flag signal, when the first sub-circuit detects that a level of the input signal is out of a first threshold of the monitoring range, and wherein the range checking circuit comprises a second sub-circuit being configured to provide the error flag signal, when the second sub-circuit detects that a level of the sampled version of the input signal is out of a second threshold of the monitoring range.

12. The electric circuitry of claim 1, wherein the signal processing circuit is configured to generate an output signal based on averaging of an amount of sampled versions of the input signal, and/or on weighted signal processing of the sampled version of the input signal, wherein the weighted signal processing is performed by different weightings in dependence on different monitoring ranges.

13. A photon counting circuitry, comprising:

a photon detector having a photon sensitive area, the photon detector being configured to generate a current signal in dependence on an impact of a photon on the photon sensitive area, a front-end electronic circuitry to receive the current signal and to provide a voltage signal in response to the current signal, an energy discriminator being connected to the front-end electronic circuitry, the energy discriminator being configured to generate a digital signal in dependence on a comparison of a level of the voltage signal with at least one threshold value, and the electric circuitry for a baseline extraction of claim 1, and wherein the energy discriminator is configured to adjust the at least one threshold value in dependence on an output signal provided by the electric circuitry for the baseline extraction.

14. A photon counting circuitry, comprising:

a photon detector having a photon sensitive area, the photon detector being configured to generate a current signal in dependence on an impact of a photon on the photon sensitive area, a front-end electronic circuitry to receive the current signal and to provide a voltage signal in response to the current signal, an energy discriminator being connected to the front-end electronic circuitry, the energy discriminator being configured to generate a digital signal in dependence on a comparison of a level of the voltage signal with at least one threshold value, and a baseline restoration circuit being connected between an input side and an output side of the front-end electronic circuitry, and wherein the baseline restoration circuit comprises the electric circuitry for the baseline extraction of claim 1.

15. A device for medical diagnostics, comprising:

a photon counting circuitry comprising:

a photon detector having a photon sensitive area, the photon detector being configured to generate a current signal in dependence on an impact of a photon on the photon sensitive area, a front-end electronic circuitry to receive the current signal and to provide a voltage signal in response to the current signal, an energy discriminator being connected to the front-end electronic circuitry, the energy discriminator being configured to generate a digital signal in dependence on a comparison of a level of the voltage signal with at least one threshold value, and an electric circuitry for a baseline extraction comprising:

an input terminal to apply an input signal, an input signal integrity detector to determine an integrity of the input signal for the baseline extraction, a sampling circuit to sample the input signal during a sampling time, and to provide a sampled version of the input signal, a signal processing circuit to process the sampled version of the input signal, and a signal processing controller to control the signal processing circuit, wherein the input signal integrity detector is configured to determine the integrity of the input signal for the baseline extraction by evaluating the input signal or the sampled version of the input signal, and wherein the signal processing controller is configured to control the signal processing circuit so that the sampled version of the input signal is processed, when the integrity of the input signal for the baseline extraction is determined by the input signal integrity detector at least during the sampling time, wherein the energy discriminator is configured to adjust the at least one threshold value in dependence on an output signal provided by the electric circuitry for the baseline extraction, and wherein the device is configured as an X-ray apparatus or a computed tomography scanner.

* * * * *